United States Patent
Song et al.

(10) Patent No.: US 12,359,213 B2
(45) Date of Patent: *Jul. 15, 2025

(54) METHOD AND USE FOR IDENTIFYING PLANT SPECIES BASED ON WHOLE GENOME ANALYSIS AND GENOME EDITING

(71) Applicant: Institute of Medicinal Plant Development (IMPLAD), CAMS & PUMC, Beijing (CN)

(72) Inventors: Jingyuan Song, Beijing (CN); Lijun Hao, Beijing (CN); Wenjie Xu, Beijing (CN); Tianyi Xin, Beijing (CN); Guihong Qi, Beijing (CN)

(73) Assignee: Institute of Medicinal Plant Development, Chinese Academy of Medical Science, Beijing (CN)

( * ) Notice: Subject to any disclaimer, the term of this patent is extended or adjusted under 35 U.S.C. 154(b) by 179 days.

This patent is subject to a terminal disclaimer.

(21) Appl. No.: 17/687,928

(22) Filed: Mar. 7, 2022

(65) Prior Publication Data

US 2023/0193301 A1 Jun. 22, 2023

Related U.S. Application Data

(63) Continuation of application No. PCT/CN2021/138005, filed on Dec. 14, 2021.

(51) Int. Cl.
| | | |
|---|---|---|
| C12N 15/82 | (2006.01) | |
| C12Q 1/6895 | (2018.01) | |
| G16B 30/00 | (2019.01) | |
| G16B 35/20 | (2019.01) | |
| G16B 99/00 | (2019.01) | |

(52) U.S. Cl.
CPC ....... *C12N 15/8213* (2013.01); *C12Q 1/6895* (2013.01); *C12N 2310/20* (2017.05); *G16B 30/00* (2019.02); *G16B 35/20* (2019.02); *G16B 99/00* (2019.02)

(58) Field of Classification Search
CPC .................................................... C12N 15/82
See application file for complete search history.

(56) References Cited

U.S. PATENT DOCUMENTS

| | | | |
|---|---|---|---|
| 11,398,294 B2* | 7/2022 | Song | C12Q 1/6869 |
| 11,584,936 B2* | 2/2023 | Mahfouz | C12N 9/22 |
| 2021/0009974 A1* | 1/2021 | Harrington | C12N 15/113 |
| 2021/0171973 A1 | 6/2021 | Chen et al. | |
| 2022/0333208 A1* | 10/2022 | Gootenberg | C12Q 1/682 |

FOREIGN PATENT DOCUMENTS

| | | | | |
|---|---|---|---|---|
| CA | 3048939 A1 | 7/2018 | | |
| CN | 110066852 A | 7/2019 | | |
| CN | 113174433 A | 7/2021 | | |
| CN | 113201586 A | 8/2021 | | |
| WO | WO-2014093622 A2 * | 6/2014 | ......... | A01K 67/0275 |
| WO | 2019128744 A1 | 7/2019 | | |
| WO | 2021068086 A1 | 4/2021 | | |

OTHER PUBLICATIONS

Collins Dictionary, Definition of Counterfeit, Collins Dictionary, 2024, 1. Obtain online at: https://www.collinsdictionary.com/us/dictionary/english/counterfeit on May 14, 2024. (Year: 2024).*
Smolander et al., Evaluation of Tools for Identifying Large Copy Number Variations from Ultra-Low-Coverage Whole-Genome Sequencing Data, BMS Genomics, May 2021, 22(357), 1-15. (Year: 2021).*
Abudayyeh et al., Nucleic Acid Detection of Plant Genes Using CRISPR-Cas13, The CRISPR Journal, 2019, 2(3), 165-171. (Year: 2019).*
Kellner et al., SHERLOCK: Nucleic Acid Detection with CRISPR Nucleases; Nature Protocols, 2019, 14, 2986-3012. (Year: 2019).*
Tian et al., CRISPR-Cas12a Based Internal Negative Control for Nonspecific Products of Exponential Rolling Circle Amplification; Nucleic Acids Research, 2020, 48(5), 1-7. (Year: 2020).*
Spink et al., Defining the Types of Counterfeiters, Counterfeiting, and Offender Organizations, Crime Science, 2013, 2(8), 1-10. (Year: 2013).*
Le Sage, Carlos, SHERLOCK: The Case of the Disruptive Diagnostic; Discovery Horizon, 2017, 1-2. Obtained online at: https://horizondiscovery.com/en/blog/2017/sherlock-the-case-of-the-disruptive-diagnostic on Dec. 18, 2024. (Year: 2017).*
Hao et al., GAGE is a Method for Identification of Plant Species Based on Whole Genome Analysis and Editing, Communications Biology, 2022, 5(947), 1-7. (Year: 2022).*
Arakawa, Hiroshi, "A method to convert mRNA into a gRNA library for CRISPR/Cas9 editing of any organism," Sci Adv, Aug. 24, 2016, 11 pages.

(Continued)

*Primary Examiner* — Amy M Bunker
(74) *Attorney, Agent, or Firm* — Ladas & Parry (57) ABSTRACT

A method for identifying plant species based on whole genome analysis and genome editing, i.e., a GAGE, includes that screening PAM-carrying sequences from a whole genome of a plant to be identified; aligning the PAM-carrying sequences with genomes of counterfeit species and closely related species, and then selecting sequences that are only present in the genome of the plant to be identified as target sequences; and performing a detection on the target sequences as selected by introducing a genome editing system, wherein based on the target sequences as selected, a CRISPR RNA (crRNA), which acts to guide a Cas protein to bind with a target sequence to form a complex, is designed and synthesized; then the trans-cleavage activity of the Cas protein is activated so that a single strand DNA bearing a fluorescent signal group is cleaved; and the plant species is identified by detecting the fluorescent signal.

4 Claims, 5 Drawing Sheets

Specification includes a Sequence Listing.

(56) References Cited

OTHER PUBLICATIONS

Zhou, Xincheng et al., "Advances of Genomics and Its Utilization in Tropical Crops," Chinese Journal of Tropical Crops, Sep. 18, 2020, 2130-2142.
Kanitchindaa, Suthasinee, "CRISPR-Cas fluorescent cleavage assay coupled with recombinase polymerase amplification for sensitive and specific detection of Enterocytozoon hepatopenaei," Biotechnology Reports, Jun. 6, 2020, 11 pages.
Bourgeois, Jacob et al., "Identification of Spacer and Protospacer Sequence Requirements in the Vibrio cholerae Type I-E CRISPR/Cas System," mSphere, Nov. 18, 2020, 13 pages.
Li, Nan et al., "Trend and Topic Analysis of Global Plant Science Research," Oct. 20, 2020, 148-159.
China First Office Action for Application No. 202180026003.0, mailed on May 11, 2023, 10 pages.
International Search Report and Written Opinion for Application No. PCT/CN2021/138005, mailed on Sep. 20, 2022, 15 pages.
Notice of Allowance dated May 26, 2023 for Application No. CN202180026003.

* cited by examiner

FIG. 1

| Classification | Total target number | Precent | Deduplicated target number |
|---|---|---|---|
| Genome | 178043117 | 100% | 59282259 |
| Unannotated regions | 151251456 | 85% | 46700437 |
| Annotated regions | 26791661 | 15% | 12581822 |
| Coding genes | 26771965 | | 16626193 |
| CDS regions | 1997115 | | 1262246 |
| Non-coding RNAs | 21275 | | 5111 |

FIG. 2

| Species | Number of mismatches | | | | | |
|---|---|---|---|---|---|---|
| | 0 | 1 | 2 | 3 | 4 | 5 |
| Crocus sativus | 201 | 13 | 8 | 0 | 4 | 61 |
| Carthamus tinctorius | 0 | 0 | 0 | 0 | 0 | 17 |
| Nelumbo nucifera | 0 | 0 | 0 | 0 | 14 | 63 |
| Zea mays | 0 | 0 | 0 | 0 | 5 | 26 |

| Chromosome | Location | Sequence (5'→3') | | Direction of strand | Number of mismatches |
|---|---|---|---|---|---|
| chr1 | 365527282 | TTTGTGCCTACTCTtCGTGTCCTTG | (SEQ ID NO: 1) | - | 1 |
| chr1 | 562319670 | TTTGTGCCTACTCTCCGTGTCCTgG | (SEQ ID NO: 2) | - | 1 |
| chr1 | 945245496 | TTTGTGCCTACTCTtCGTGTCCTTG | (SEQ ID NO: 3) | - | 1 |
| chr1 | 945453723 | TTTGTGCCTACTCTcGTGTCCTTG | (SEQ ID NO: 4) | - | 1 |
| chr2 | 16933964 | TTTGTGCCTACTCTCCGTGTCCTTc | (SEQ ID NO: 5) | + | 1 |
| chr2 | 9025836 | TTTGTGCCTACTCTCCGTGTCCcTG | (SEQ ID NO: 6) | - | 1 |
| chr3 | 729719 | TTTGTGCCTACTCTCCGcGTCCTTG | (SEQ ID NO: 7) | - | 1 |
| chr3 | 746190 | TTTGTGCCTACTCTCCGcGTCCTTG | (SEQ ID NO: 8) | + | 1 |
| chr6 | 208473188 | TTTGTGCCTACgCTCCGTGTCCTTG | (SEQ ID NO: 9) | + | 1 |
| chr6 | 209771094 | TTTGTGCCTACgCTCCGTGTCCTTG | (SEQ ID NO: 10) | + | 1 |
| chr8 | 127085844 | TTTGTGCCTACTCTCCGTGTCaTTG | (SEQ ID NO: 11) | - | 1 |
| chr8 | 65165634 | TTTGTGCCTACTCTtCGTGTCCTTG | (SEQ ID NO: 12) | + | 1 |
| chr8 | 65184893 | TTTGTGCCTACTCTcGTGTCCTTG | (SEQ ID NO: 13) | + | 1 |
| chr1 | 560187580 | TTTGTGCCTACTCTtCGTGTCCTgG | (SEQ ID NO: 14) | - | 2 |
| chr2 | 50064681 | TTTGTGCCcACTCTCCGTGTCCTTt | (SEQ ID NO: 15) | + | 2 |
| chr2 | 79230269 | TTTGTGCCcACTCTCCGTGTCCTTt | (SEQ ID NO: 16) | - | 2 |
| chr3 | 518276986 | TTTGTGCCTACTCTCCGTGTCCTgc | (SEQ ID NO: 17) | - | 2 |
| chr5 | 448736026 | TTTGTGCCTACTCTagGTGTCCTTG | (SEQ ID NO: 18) | + | 2 |
| chr5 | 449535986 | TTTGTGCCTACTCTggGTGTCCTTG | (SEQ ID NO: 19) | + | 2 |
| chr5 | 449948285 | TTTGTGCCTACTCTagGTGTCCTTG | (SEQ ID NO: 20) | - | 2 |
| tig00095233_pilon187 | | TTTGTGCCTACTCTCCGTGTCCTgc | (SEQ ID NO: 21) | - | 2 |

SEQUENCE LISTING

```
<160> NUMBER OF SEQ ID NOS: 27

<210> SEQ ID NO 1
<211> LENGTH: 25
<212> TYPE: DNA
<213> ORGANISM: Crocus sativus
<220> FEATURE:
<221> NAME/KEY: misc_feature
<223> OTHER INFORMATION: chr1

<400> SEQUENCE: 1
tttgtgccta ctcttcgtgt ccttg                                       25

<210> SEQ ID NO 2
<211> LENGTH: 25
<212> TYPE: DNA
<213> ORGANISM: Crocus sativus
<220> FEATURE:
<221> NAME/KEY: misc_feature
<223> OTHER INFORMATION: chr1
```

```
<400> SEQUENCE: 2
tttgtgccta ctctccgtgt cctgg                                              25

<210> SEQ ID NO 3
<211> LENGTH: 25
<212> TYPE: DNA
<213> ORGANISM: Crocus sativus
<220> FEATURE:
<221> NAME/KEY: misc_feature
<223> OTHER INFORMATION: chr1

<400> SEQUENCE: 3
tttgtgccta ctcttcgtgt ccttg                                              25

<210> SEQ ID NO 4
<211> LENGTH: 25
<212> TYPE: DNA
<213> ORGANISM: Crocus sativus
<220> FEATURE:
<221> NAME/KEY: misc_feature
<223> OTHER INFORMATION: chr1

<400> SEQUENCE: 4
tttgtgccta ctctctgtgt ccttg                                              25

<210> SEQ ID NO 5
<211> LENGTH: 25
<212> TYPE: DNA
<213> ORGANISM: Crocus sativus
<220> FEATURE:
<221> NAME/KEY: misc_feature
<223> OTHER INFORMATION: chr2

<400> SEQUENCE: 5
tttgtgccta ctctccgtgt ccttc                                              25

<210> SEQ ID NO 6
<211> LENGTH: 25
<212> TYPE: DNA
<213> ORGANISM: Crocus sativus
<220> FEATURE:
<221> NAME/KEY: misc_feature
<223> OTHER INFORMATION: chr2

<400> SEQUENCE: 6
tttgtgccta ctctccgtgt ccctg                                              25

<210> SEQ ID NO 7
<211> LENGTH: 25
<212> TYPE: DNA
<213> ORGANISM: Crocus sativus
<220> FEATURE:
<221> NAME/KEY: misc_feature
<223> OTHER INFORMATION: chr3

<400> SEQUENCE: 7
tttgtgccta ctctccgcgt ccttg                                              25

<210> SEQ ID NO 8
<211> LENGTH: 25
<212> TYPE: DNA
<213> ORGANISM: Crocus sativus
<220> FEATURE:
<221> NAME/KEY: misc_feature
<223> OTHER INFORMATION: chr3
```

<400> SEQUENCE: 8
tttgtgccta ctctccgcgt ccttg                                    25

<210> SEQ ID NO 9
<211> LENGTH: 25
<212> TYPE: DNA
<213> ORGANISM: Crocus sativus
<220> FEATURE:
<221> NAME/KEY: misc_feature
<223> OTHER INFORMATION: chr6

<400> SEQUENCE: 9
tttgtgccta cgctccgtgt ccttg                                    25

<210> SEQ ID NO 10
<211> LENGTH: 25
<212> TYPE: DNA
<213> ORGANISM: Crocus sativus
<220> FEATURE:
<221> NAME/KEY: misc_feature
<223> OTHER INFORMATION: chr6

<400> SEQUENCE: 10
tttgtgccta cgctccgtgt ccttg                                    25

<210> SEQ ID NO 11
<211> LENGTH: 25
<212> TYPE: DNA
<213> ORGANISM: Crocus sativus
<220> FEATURE:
<221> NAME/KEY: misc_feature
<223> OTHER INFORMATION: chr8

<400> SEQUENCE: 11
tttgtgccta cgctccgtgt cattg                                    25

<210> SEQ ID NO 12
<211> LENGTH: 25
<212> TYPE: DNA
<213> ORGANISM: Crocus sativus
<220> FEATURE:
<221> NAME/KEY: misc_feature
<223> OTHER INFORMATION: chr8

<400> SEQUENCE: 12
tttgtgccta cgcttcgtgt ccttg                                    25

<210> SEQ ID NO 13
<211> LENGTH: 25
<212> TYPE: DNA
<213> ORGANISM: Crocus sativus
<220> FEATURE:
<221> NAME/KEY: misc_feature
<223> OTHER INFORMATION: chr8

<400> SEQUENCE: 13
tttgtgccta ctctctgtgt ccttg                                    25

<210> SEQ ID NO 14
<211> LENGTH: 25
<212> TYPE: DNA
<213> ORGANISM: Crocus sativus
<220> FEATURE:
<221> NAME/KEY: misc_feature
<223> OTHER INFORMATION: chr1

<400> SEQUENCE: 14
tttgtgccta ctcttcgtgt cctgg                                       25

<210> SEQ ID NO 15
<211> LENGTH: 25
<212> TYPE: DNA
<213> ORGANISM: Crocus sativus
<220> FEATURE:
<221> NAME/KEY: misc_feature
<223> OTHER INFORMATION: chr2

<400> SEQUENCE: 15
tttgtgccca ctctccgtgt cctttt                                      25

<210> SEQ ID NO 16
<211> LENGTH: 25
<212> TYPE: DNA
<213> ORGANISM: Crocus sativus
<220> FEATURE:
<221> NAME/KEY: misc_feature
<223> OTHER INFORMATION: chr2

<400> SEQUENCE: 16
tttgtgccca ctctccgtgt cctttt                                      25

<210> SEQ ID NO 17
<211> LENGTH: 25
<212> TYPE: DNA
<213> ORGANISM: Crocus sativus
<220> FEATURE:
<221> NAME/KEY: misc_feature
<223> OTHER INFORMATION: chr3

<400> SEQUENCE: 17
tttgtgccta ctctccgtgt cctgc                                       25

<210> SEQ ID NO 18
<211> LENGTH: 25
<212> TYPE: DNA
<213> ORGANISM: Crocus sativus
<220> FEATURE:
<221> NAME/KEY: misc_feature
<223> OTHER INFORMATION: chr5

<400> SEQUENCE: 18
tttgtgccta ctctaggtgt ccttg                                       25

<210> SEQ ID NO 19
<211> LENGTH: 25
<212> TYPE: DNA
<213> ORGANISM: Crocus sativus
<220> FEATURE:
<221> NAME/KEY: misc_feature
<223> OTHER INFORMATION: chr5

<400> SEQUENCE: 19
tttgtgccta ctctgggtgt ccttg                                       25

<210> SEQ ID NO 20
<211> LENGTH: 25
<212> TYPE: DNA
<213> ORGANISM: Crocus sativus
<220> FEATURE:
<221> NAME/KEY: misc_feature
<223> OTHER INFORMATION: chr5

<400> SEQUENCE: 20
tttgtgccta ctctaggtgt ccttg                                          25

<210> SEQ ID NO 21
<211> LENGTH: 25
<212> TYPE: DNA
<213> ORGANISM: Crocus sativus
<220> FEATURE:
<221> NAME/KEY: misc_feature
<223> OTHER INFORMATION: tig00095233_pilon

<400> SEQUENCE: 21
tttgtgccta ctctccgtgt cctgc                                          25

<210> SEQ ID NO 22
<211> LENGTH: 35
<212> TYPE: DNA
<213> ORGANISM: Crocus sativus
<220> FEATURE:
<221> NAME/KEY: misc_feature
<223> OTHER INFORMATION: Cs_target1

<400> SEQUENCE: 22
cgttgtttgt gcctactctc cgtgtccttg ccctc                               35

<210> SEQ ID NO 23
<211> LENGTH: 42
<212> TYPE: RNA
<213> ORGANISM: Artificial Sequence
<220> FEATURE:
<223> OTHER INFORMATION: Synthetic: Cs_crRNA

<400> SEQUENCE: 23
uuaauucuac uaaugguaga uugccuacuc uccguguccu ug                       42

<210> SEQ ID NO 24
<211> LENGTH: 19
<212> TYPE: DNA
<213> ORGANISM: Artificial Sequence
<220> FEATURE:
<223> OTHER INFORMATION: Synthetic: PCR Primer

<400> SEQUENCE: 24
atggcgtttt gtgacgaag                                                 19

<210> SEQ ID NO 25
<211> LENGTH: 20
<212> TYPE: DNA
<213> ORGANISM: Artificial Sequence
<220> FEATURE:
<223> OTHER INFORMATION: Synthetic: PCR Primer

<400> SEQUENCE: 25
ctaggaggtg tgtgtgggga                                                20

<210> SEQ ID NO 26
<211> LENGTH: 10
<212> TYPE: DNA
<213> ORGANISM: Artificial Sequence
<220> FEATURE:
<223> OTHER INFORMATION: Synthetic: Poly-A
<220> FEATURE:
<221> NAME/KEY: misc_feature
<223> OTHER INFORMATION: 5' FAM and 3' BHQ

<400> SEQUENCE: 26
aaaaaaaaaa                                                           10

```
<210> SEQ ID NO 27
<211> LENGTH: 35
<212> TYPE: DNA
<213> ORGANISM: Artificial Sequence
<220> FEATURE:
<223> OTHER INFORMATION: Synthetic

<400> SEQUENCE: 27
gagggcaagg acacggagag taggcacaaa caacg                                35
```

# METHOD AND USE FOR IDENTIFYING PLANT SPECIES BASED ON WHOLE GENOME ANALYSIS AND GENOME EDITING

CROSS-REFERENCE TO RELATED APPLICATIONS

This application is a continuation of International Application No. PCT/CN2021/138005, filed on Dec. 14, 2021, the entire disclosure of which is incorporated herein by reference.

REFERENCE TO SEQUENCE LISTING SUBMITTED VIA EFS-WEB

This application includes an electronically submitted sequence listing in .txt format. The .txt file contains a sequence listing entitled "2022-07-02U_021000-3_ST25.txt" created on Jul. 2, 2022 and is 5,732 bytes in size. The sequence listing contained in this txt file is part of the specification and is hereby incorporated by reference herein in its entirety.

TECHNICAL FIELD

The present disclosure relates to the field of identification technologies of plant species, and in particular to a method and use for identifying plant species based on whole genome analysis and genome editing.

BACKGROUND

Identification of plant species has been closely linked with nature exploration, social development, and scientific research since the dawn of human societies. Although the total number of plants on the earth has not been determined yet, there is no doubt that this is an enormous number. Thus, the identification and classification of the variety of plants that are distributed widely and difficult to be identified are a long-term and arduous task. In early stage of the research, species identification was mainly made based on the phenotypes of plants such as morphological characteristics, chemical ingredients or the like. However, the phenotypes of plants are influenced by factors like the environment or growing stage, and are generally incapable of reflecting the nature, i.e., the genotype, of plants. Since the 1980s, the introduction of DNA sequencing data had made the genotype-based plant species identification become possible. As a carrier of the whole genetic information of a plant, the whole genome is an ideal database for plant identification, and the identification based on the whole genome is a future trend of this field. In the past, due to limitations such as lack of whole genome resources or poor abilities in analyzing biological information, molecular biological identification methods like DNA barcoding technology merely keep a focus on several specific regions, which fails to exploit and utilize the potential of the whole genome in species identification.

With the continuous developments of the sequencing techniques, more and more whole genomes of plants have been reported. Also, the development of computer science including software and hardware has greatly enhanced the ability in analyzing the genomes. Both developments provide a strong support for implementing the plant identification on a whole genome scale.

Clustered regularly interspaced short palindromic repeats (CRISPR)/CRISPR-associated proteins (CRISPR/Cas) system has attracted great attentions since its advent. Besides the application in genome editing, the discovery and application of the trans-cleavage activity of Cas12a and Cas13a have introduced the CRISPR/Cas system into the species identification field. Methods like DETECTR, SHERLOCK and HOLMES were developed by Jennifer A. Doudna, Feng Z., Jin W., et al, and then successfully applied to the detection and identification of virus and bacteria. In the CRISPR/Cas12a system, the crRNA can recognize a targeting sequence in a specific manner and guide the Cas12 to bind with the targeting sequence to form a ternary complex. Then the trans-cleavage activity of the Cas12 is activated, cleaving the fluorescent signal molecule to produce fluorescence which can be detected. Such reaction is carried out at 37° C., which is easy to operate and only requires a constant temperature condition and a fluorescence detection instrument.

However, target sequences carrying a protospacer adjacent motif (PAM) can only be screened from specific gene regions due to the technical limitations in the related art. Owing to the small scale of the gene database for screen, the target sequences that can be obtained are quite limited in number, which leads to insufficient specificity of the target sequences and thereby likely occurrence of errors such as off-target. As a result, demands for identifying different species cannot be sufficiently satisfied. As the whole genome contains the entire genetic information of an organism and is an ideal database for species identification, screening differences in sequence via whole genome alignment and conducting a further identification on this basis are future trends of this field. The present disclosure (hereinafter referred to as a GAGE method) has combined whole genome analysis with genome editing strategy, which achieves plant species identification on a whole genome scale for the first time. Compared with the prior art, the GAGE method is capable of obtaining, by screening PAM-carrying target sequences from the whole genome, all PAM-carrying target sequences of the plant to be identified that may possibly be used in species identification, which has sufficiently exploited the application potential of the whole genome in species identification, and provided adequate candidate target sequences for the selection of the specific PAM-carrying target sequences that are used for determining the identity between the plant to be detected and the plant to be identified during the subsequent alignment with the genome of the plant to be identified. Given the massive amount of information contained in the genome and the wide range of the distribution of the PAM-carrying target sequences, theoretically, the GAGE method can screen and obtain all specific PAM-carrying target sequences that can be used for determining the identity between any plant to be detected and the plant to be identified, thereby avoiding the risk of errors such as off-target, namely, the GAGE method can accurately determine the identity between any plant to be detected and the plant to be identified.

SUMMARY

To this end, the present disclosure provides a method for identifying plant species based on whole genome analysis and genome editing. The method includes the following steps:

step 1, constructing a small-fragment genomic library based on a whole genome of a plant to be identified. In some embodiments, the whole genome of the plant to be identified is divided into (L−K+1) fragments each having a length of K to form the small-fragment genomic library; copy numbers of the respective fragments are calculated, and then genomic position of each fragment is determined by aligning the fragment with the genome, where L represents a length of the genome and K represents the length of each fragment in the library;

step 2, extracting candidate target sequences each carrying a PAM from the whole genome of the plant to be identified, wherein the PAM (protospacer adjacent motif) can be determined according to a genome editing system as selected. For example, for a CRISPR/Cas12a system, a motif with TTTV at the 5' end or VAAA at the 3' end may be selected. Such knowledge is well known to those skilled in the art and thus is not repeated here. Preferably, each fragment in the small-fragment genomic library is detected for the PAM motif, and the candidate target sequences carrying the PAM are extracted to construct a candidate target sequences library;

step 3, aligning the candidate target sequences with whole genomes of counterfeit species and closely related species for screen, and selecting sequences that are only present in the plant to be identified, preferably the candidate target sequences located in a region with high intra-species conservation and high inter-species variability, as target sequences. Considering the off-target effect, it is preferable that the genomes of the counterfeit species and the closely related species do not contain any sequence which has at most n different bases from the target sequences as selected, where n is greater than or equal to 3. Preferably, the specificity of the target sequences can be further improved by increasing the value of n, or, a predetermined number range of target sequences can be obtained via the screen by adjusting the value of n;

step 4, designing and synthesizing CRISPR RNA (crRNA) according to the selected genome editing system based on the screened target sequences. Preferably, a target sequences library and a crRNA sequences library matching the target sequences library of the plant to be identified relative to its counterfeit species and closely related species can be constructed by repeating step 3 and step 4;

step 5, extracting genomic DNA of a plant to be detected, and amplifying and recovering the target sequences as a DNA substrate or directly using the extracted genomic DNA of the plant to be detected as the DNA substrate. For example, the genomic DNA of the plant to be detected may be amplified with primers which can specifically amplify the target sequences, and then the target sequences are recovered as the DNA substrate; or, the genomic DNA of the plant to be detected can be amplified with primers which can specifically amplify DNA sequences containing the target sequences, and then the DNA sequences containing the target sequences are recovered as the DNA substrate; and step 6, according to the selected genome editing system, carrying out a reaction with at least 6 ingredients comprising a buffer, a Cas protein, the crRNA, nuclease-free water, the DNA substrate and fluorescent signal molecule such as an ssDNA reporter (fluorescent reporter gene).

Specifically, the buffer and the Cas protein can be determined according to the selected genome editing system. Taking the CRISPR/Cas12a system as an example, the NEBuffer 2.1 and Lba Cas12a (Cpf1) may be selected, Poly_A_FQ (5'-FAM-AAAAAAAAAA-BHQ-3')(SEQ ID NO: 26) may be selected as the fluorescent signal molecule, and the reaction condition may be as follows:

| 5.1 The reaction system is as follows. | |
|---|---|
| Ingredient | Volume |
| Nuclease-free H$_2$O | 71 μL |
| 10 × NEBuffer 2.1 | 10 μL |
| Lba Cas12a (Cpf1) | 2 μL (20 nM) |
| crRNA | 3 μL (300 nM) |

5.2 The reaction system is incubated at room temperature for 30 minutes.

5.3.1 The amplified and recovered target sequences are used as the DNA substrate.

10 μL of the amplified and recovered target sequences (1 ng/μL) and 4 μL Poly_A_FQ (400 nM) are added, and then incubated at 37° C. and detected with a microplate reader for fluorescence value at $\lambda_{ex}$ 483 nm/$\lambda_{em}$ 535 nm (determined based upon the selected fluorescent signal molecule), at the time points of 0, 3, 6, 9, 12, 15, 25, 35, 45, and 60 minutes, respectively.

5.3.2 The genomic DNA is used as a DNA substrate.

10 μL of the genomic DNA (10 ng/μL) and 4 μL Poly_A_FQ (400 nM) are added, and then incubated at 37° C. for 60 min, and then further incubated at 37° C. and detected with the microplate reader for fluorescence value at $\lambda_{ex}$ 483 nm/$\lambda_{em}$ 535 nm (determined based upon the selected fluorescent signal molecule), at the time points of 0, 3, 6, 9, 12, 15, 25, 35, 45, 60, 75, 105, 135, and 165 minutes, respectively.

If the detection result has a significant difference (P<0.01) from the blank control, it can be determined that there is identical between the plant to be detected and the plant to be identified, otherwise, it is determined that there is nonidentical between the plant to be detected and the plant to be identified.

The GAGE method of the present disclosure will now be described in further detail with reference to the accompanying drawings to fully explain the purpose, the technical features, and the technical effects of the present disclosure.

BRIEF DESCRIPTION OF THE DRAWINGS

To describe the technical solutions of the present disclosure or the related art more clearly, the following briefly introduces the accompanying drawings required for describing the embodiments or the related art. However, the accompanying drawings in the following show merely some embodiments of the present disclosure and are not intended to limit the protection scope of the present disclosure.

FIG. 3 (SEQ ID NOS: 1-21) shows a diagram illustrating the specificity analysis of the target sequences.

DETAILED DESCRIPTION OF THE EMBODIMENTS

Figure 1:
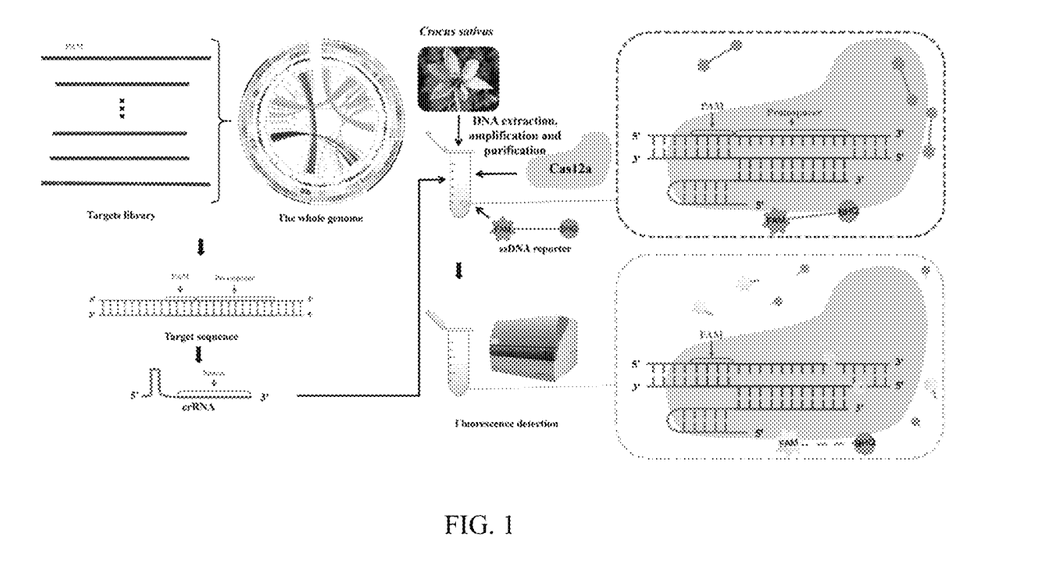
FIG. 1 shows the flowchart of the GAGE method of the present disclosure.

FIG. 1 shows the flowchart of the GAGE method of present disclosure. In combination with the identification process of *Crocus sativus* as detailed examples, the GAGE method of present disclosure is further explained. The experimental methods of which the specific conditions are not specified in the following examples are all implemented under conventional conditions.

Example 1: Construction of a Small-Fragment Genomic Library and a Target Sequences Library of *Crocus sativus*

The *Crocus sativus*, derived from dried stigma of *Crocus sativus*, Iridaceae family, is a premium traditional Chinese medicine having the therapeutic effects including promoting blood circulation and removing stasis, removing pattogenic heat from the blood and toxic material from the body, relieving stress and comforting minds, or the like. Besides its medicinal application, *Crocus sativus* is also used as a coloring agent and spice for food, having the reputation of "red gold". The counterfeit species of the *Crocus sativus* mainly include *Carthamus tinctorius, Nelumbo nucifera, Zea mays* and so on.

1.1 Construction of the Small-Fragment Genomic Library of *Crocus sativus*

The whole genome of *Crocus sativus* was selected and divided into (L−25+1) fragments each having a length of 25 bp using the Jellyfish (v1.1.12), so as to construct the small-fragment genomic library, where L represents the length of the genome.

1.2 Construction of the Candidate Target Sequences Library of *Crocus sativus*

Figure 2:
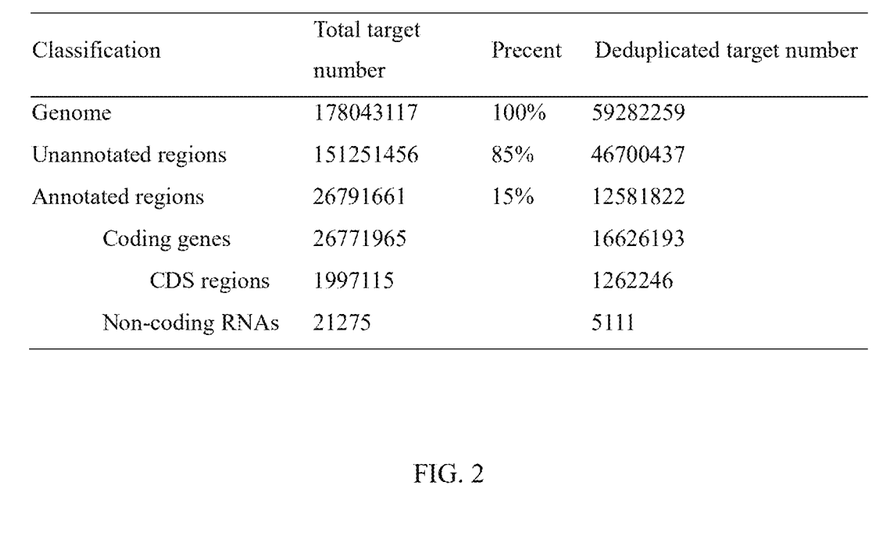
FIG. 2 shows a candidate target sequences library of *Crocus sativus*.

The candidate target sequences library was constructed by extracting sequences each carrying a PAM (the CRISPR/Cas12a system was used in this example, with 5' end of the PAM bearing TTTV or 3' end bearing VAAA) from the small-fragment genomic library of *Crocus sativus*. As a result, 178,043,117 candidate target sequences were totally screened from the whole genome of *Crocus sativus*, with 59,282,259 remained after deduplication. According to the genomic annotation information, about 85% of the candidate target sequences were located in annotated regions, and 15% were located in non-annotated regions. In addition, a total number of 26,771,965 target sequences were located in encoding regions, and 21,275 were located in non-encoding regions. Among those located in the encoding regions, 1,997,115 target sequences were located in protein-encoding regions, as shown in FIG. 2.

Example 2: Selection of Target Sequences Used for Identifying *Crocus sativus*

2.1 Screen of Target Sequences

The screen was performed based on the following two principles: (1) the target sequences should be screened from regions with high intra-species conservation and high inter-species variability; and (2) the genomes of the counterfeit species do not contain any sequence which differs at most n bases from the screened target sequences, where n is greater than or equal to 3.

The detailed steps of the screen included: (1) data preparation: downloading all published sequences of *Crocus sativus* and sequences of whole genomes of the counterfeit species, including *Carthamus tinctorius, Nelumbo nucifera*, and *Zea mays*, from NCBI database; (2) screen of intra-species conservative candidate targets of *Crocus sativus*: aligning the candidate target sequences of *Crocus sativus* obtained from 1.2 with the sequences of *Crocus sativus* downloaded from the database using Bowtie (v1.1.0), and screening the sequences that are perfectly matched as the intra-species conservative candidate target sequences of *Crocus sativus*; and (3) screen of inter-species specific candidate targets of *Crocus sativus* aligning the candidate target sequences obtained from (2) with the genomes of the counterfeit species of the *Crocus sativus* using Bowtie (v1.1.0), and screening the sequences of *Crocus sativus* which have at least 3 mismatched bases from the counterfeit species as the selected target sequences library, FIG. 3 shows a diagram analyzing the selected target sequences library.

Figure 4:
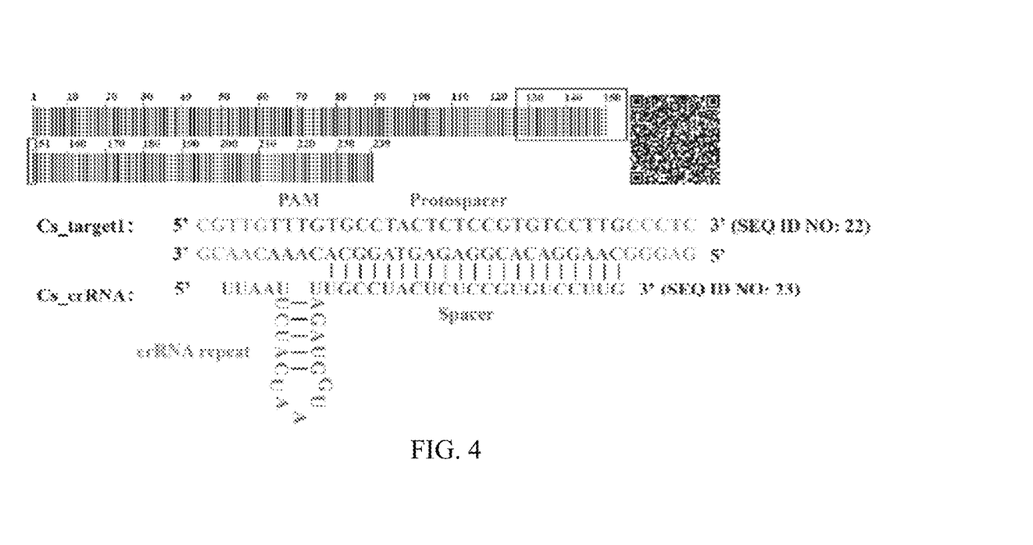
FIG. 4 (SEQ ID NOS: 22, 27 and 23) shows a target sequence in ITS2 region of *Crocus sativus* and its matching crDNA.

In this example, a target sequence was chosen from the selected target sequences library, and named Cs_target1. As shown in FIG. 4, the Cs_target1 was located in the ITS2 region of *Crocus sativus*.

2.2 Design of crRNAs Matching the Target Sequences

According to the selected genome editing system and the design principle of crRNAs, a crRNA matching the Cs_target1 was designed and named Cs_crRNA, as shown in FIG. 4.

Example 3: Amplification and Purification of the Target Sequences 3.1 Extraction of Plant DNA The *Crocus sativus* was collected from Dingzhou, Hebei province. The *Carthamus tinctorius* was collected from Wulumuqi, Xinjiang province. The *Nelumbo nucifera* was collected from botanic garden in Beijing Institute of Medicinal Plant Development. The *Zea mays* was collected from Nanning, Guangxi province. The plant samples were grinded using a ball grinder, and the total DNA was extracted according to the instructions of Plant Genomic DNA Kit provided by TIANGEN company. The integrity of the total DNA was checked with 0.8% agarose gel electrophoresis, and the purity and concentration of the total DNA were determined with a Nanodrop 2000C spectrophotometer.

3.2 Amplification of the Target Sequences

As universal primers were present in the ITS2 region where the target sequences were located, the universal primers were directly used for amplifying and purifying the target sequences. The sequences of the primers were as follows:

Forward primer P1: 5'-ATGGCGTTTTGTGACGAAG-3' (SEQ ID NO: 24); and

Reverse primer P2: 5'-CTAGGAGGTGTGTGTGGGGA-3' (SEQ ID NO: 25).

The total volume of the PCR reaction was 50 μL: 25 μL 2×Taq MasterMix, 2 μL primer (F/R) (10 μM), 2 μL total DNA samples, with a balance of nuclease-free $H_2O$ to make the final volume 50 μL. The condition of the PCR reaction is: 95° C. 30 S; 35 cycles: 95° C. 5 sec, 58° C. 30 sec, and 72° C. 2 min; and 72° C. 10 min; and 10° C. for storage.

3.3 Purification and Recovery of the PCR Products

The PCR products were recovered and purified according to the instructions of Universal DNA Purification Kit provided by TIANGEN company. The integrity of the target sequences was checked with 2% agarose gel electrophoresis, and the purity and concentration of the target sequences were determined with the Nanodrop 2000C spectrophotometer. Then the recovered ITS2 fragments were used as the DNA substrate for subsequent experiments.

Example 4: Identification of *Crocus sativus* by Using the GAGE Method

Group Cs (*Crocus sativus*), Group Ct (*Carthamus tinctorius*), Group Zm (*Nelumbo nucifera*), Group Nn (*Zea mays*) and Group CK (blank control) were set up by using Cs_crRNA as crRNA and using ITS2 fragments of *Crocus sativus*, *Carthamus tinctorius*, *Nelumbo nucifera*, and *Zea mays* as the DNA substrates. Experiments were carried out by using EnGen Lba Cas12a (Cpf1) from NEB company, with a total reaction volume of 100 µL: 10 µL 10×NEBuffer 2.1, 2 µL Lba Cas12a (20 nM), 3 µL Cs_crRNA (300 nM), 10 µL DNA substrate (1 ng/µL), 4 µL Poly_A_FQ (400 nM) and 71 µL nuclease-free $H_2O$. The reaction system was first added with NEBuffer 2.1, Lba Cas12a, Cs_crRNA and nuclease-free $H_2O$, incubated at room temperature for 30 minutes, and then added with DNA substrate and Poly_A_FQ, incubated at 37° C. and detected with the microplate reader for fluorescence at $\lambda_{ex}$ 483 nm/$\lambda_{em}$ 535 nm, at the time points of 0, 3, 6, 9, 12, 15, 25, 35, 45, and 60 minutes, respectively.

Figure 5:
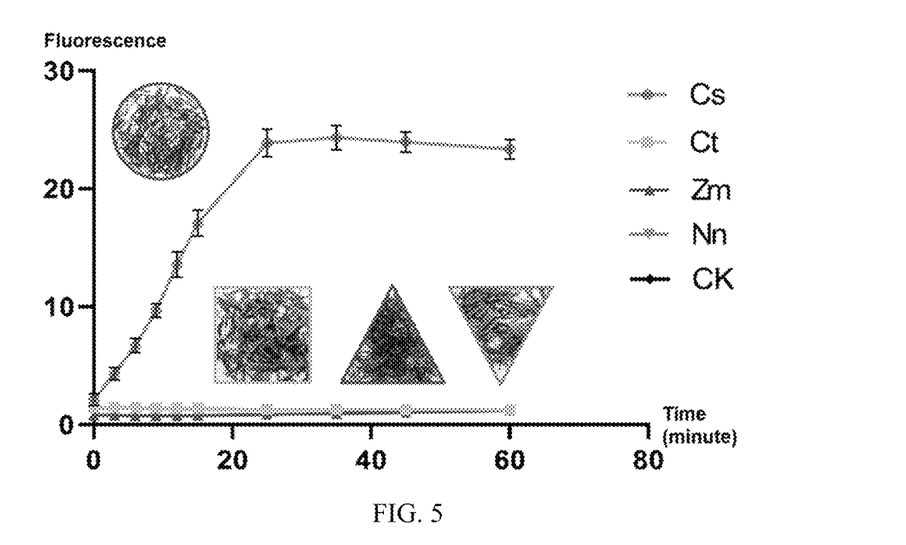
FIG. 5 shows a result of fluorescence detection when applying the GAGE method of present disclosure to *Crocus sativus*.

As seen from the results shown in FIG. 5, only Group Cs produced a fluorescent signal, and the fluorescence value reached the maximum at about 25 minutes and maintained there, which had a significant difference from Group CK (P>0.01). In addition, Group Ct, Group Zm, and Group Nn were consistent with Group CK, generating no fluorescence signal at all, and the fluorescence values thereof did not have a significant difference from Group CK (P<0.01). The results indicated that the GAGE method can accurately and conveniently identify the *Crocus sativus*.

Example 5: Identification of *Crocus sativus* by Directly Using Genomic DNA

Group Cs*, Group Ct*, Group Zm*, Group Nn*, and Group CK were set up by using Cs_crRNA as crRNA and using genomic DNAs of *Crocus sativus*, *Carthamus tinctorius*, *Nelumbo nucifera*, and *Zea mays* as DNA substrates, respectively. Experiments were carried out by using EnGen Lba Cas12a (Cpf1) from NEB company, with a total reaction volume of 100 µL: 10 µL 10×NEBuffer 2.1, 2 µL Lba Cas12a (20 nM), 3 µL Cs_crRNA (300 nM), 10 µL DNA substrate (10 ng/µL), 4 µL Poly_A_FQ (400 nM) and 71 µL nuclease-free $H_2O$. The reaction system was first added with NEBuffer 2.1, Lba Cas12a, Cs_crRNA and nuclease-free $H_2O$, incubated at room temperature for 30 minutes, and then added with DNA substrate and Poly_A_FQ, incubated at 37° C. for 60 minutes. Then the reaction system was incubated at 37° C. and detected with the microplate reader for fluorescence at $\lambda_{ex}$ 483 nm/$\lambda_{em}$ 535 nm, at the time points of 0, 3, 6, 9, 12, 15, 25, 35, 45, 60, 75, 105, 135, and 165 minutes, respectively.

Figure 6:
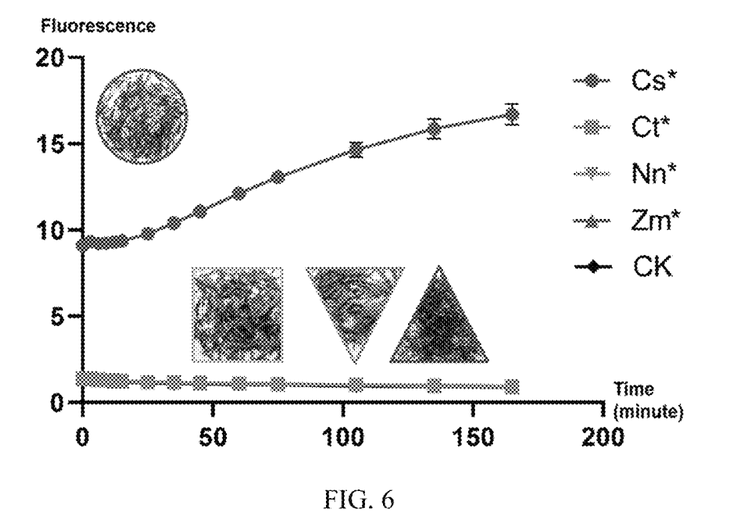
FIG. 6 shows a result of fluorescence detection when using the genomic DNA of a plant to be detected as a DNA substrate to identify *Crocus sativus*.

As seen from the results shown in FIG. 6, only Group Cs* produced a fluorescent signal, and the fluorescence value increased with time, which had a significant difference from Group CK (P>0.01). In addition, Group Ct*, Group Zm*, and Group Nn* were consistent with Group CK, generating no fluorescent signal at all, and the fluorescence values thereof did not have a significant difference from Group CK (P<0.01). The results indicated that through the GAGE method, the identification of *Crocus sativus* can be accurately and conveniently conducted by directly using the genomic DNA without an amplifying procedure.

Those of ordinary skill in the art should understand that the discussions of any of the above embodiments are only exemplary, and are not intended to imply that the protection scope of the present disclosure is limited to these embodiments. With the concept of the present disclosure, the above embodiments or technical features in different embodiments can also be combined, the steps can be implemented in any order, and there exist many other variations of the different aspects of the embodiments of the present disclosure as described above, which are not provided in detail for the sake of brevity. The embodiments of the present disclosure are intended to encompass all such substitutions, modifications and variations that fall within the broad scope of the appended claims. Therefore, any omission, modification, equivalent substitution, improvement, etc. made within the spirit and principle of the embodiments of the present disclosure should be included within the protection scope of the present disclosure.

---

What is claimed is:

1. A method for identifying plant species based on whole genome analysis and genome editing, the method comprising:
- step 1, constructing a fragment genomic library based on a sequence of a whole genome of a first plant species, wherein constructing the fragment genomic library in step 1 comprises: dividing the whole genome of the first plant species into L−K+1 fragments each having a length of K, the L−K+1 fragments constituting the fragment genomic library; calculating copy numbers of the L−K+1 fragments, and then determining genomic position of each fragment by aligning each fragment with the whole genome of the first plant species, wherein L represents a length of the whole genome and K represents the length of each fragment in the fragment genomic library;
- step 2, constructing a candidate target sequence library by extracting candidate target sequences each carrying a protospacer adjacent motif (PAM) from the fragment genomic library;
- step 3, aligning the candidate target sequences with whole genomes of at least one second plant species, and selecting any candidate target sequences that are only present in the first plant species as target sequences, wherein step 3 further comprises: aligning the candidate target sequences obtained from step 2 with the whole genome of each at least one second plant species, wherein the target sequences as selected contain at least number (n) of different bases as compared with any sequence equal in length to the target sequences from the whole genome of each of the at least one second plant species, wherein n is greater than or equal to 3;
- step 4, designing and synthesizing Clustered Regularly Interspaced Short Palindromic Repeats (CRISPR) RNAs based on the target sequences;
- step 5, extracting genomic DNA of a plant to be detected wherein the plant to be detected is a plant sample of the first plant species, the second plant species, or a species other than the first plant species and the second plant species;
- step 6, amplifying and recovering the target sequences as a DNA substrate or directly using the extracted genomic DNA of the plant to be detected as a DNA substrate;
- step 7, selecting a genome editing system selected from the group consisting of a CRISPR/Cas12a system or a CRISPR/Cas13a system;
- step 8, according to a selected genome editing system of step 7, carrying out a reaction with at least six (6) ingredients comprising: a buffer, a CRISPR-associated protein (Cas), the CRISPR RNAs (crRNAs), nuclease-free water, the DNA substrate of the plant to be detected, and single-stranded DNA (ssDNA) fluorescent reporter gene;
- step 9, performing a fluorescence detection, wherein a Cas is guided by the crRNAs to recognize and combine with the target sequences to form a ternary complex, the trans-cleavage activity of the Cas is activated to cut the ssDNA fluorescent reporter gene, such that an emitted fluorescence can be detected; and
- step 10, determining that the species of plant to be detected is the first plant species when a result of the fluorescence detection has a significant difference of $P<0.01$ from a blank control without the DNA substrate, and otherwise, determining that the species of the plant to be detected is not the first plant species.

2. The method according to claim 1, wherein step 2 further comprises screening for PAM motif in each fragment of the fragment genomic library and constructing the candidate target sequences library by extracting the candidate target sequences carrying the PAM.

3. The method according to claim 1, wherein n is adjusted.

4. The method according to claim 1, wherein step 5 further comprises: amplifying the genomic DNA of the plant to be detected with primers which specifically amplify the target sequences, and recovering the target sequences as a DNA substrate; or, amplifying the genomic DNA of the plant to be detected with primers which specifically amplify DNA sequences containing the target sequences, and recovering the DNA sequences containing the target sequences as a DNA substrate.

\* \* \* \* \*